United States Patent [19]

Bam et al.

[11] Patent Number: 5,424,467
[45] Date of Patent: Jun. 13, 1995

[54] METHOD FOR PURIFYING ALCOHOL ESTERS

[75] Inventors: Narendra Bam, New Haven, Conn.; David C. Drown, Moscow, Id.; Roger Korus, Moscow, Id.; Dwight S. Hoffman, Moscow, Id.; Timothy G. Johnson, Kenai, Ak.; Jacqueline M. Washam, Moscow, Id.

[73] Assignee: Idaho Research Foundation, Moscow, Id.

[21] Appl. No.: 92,198

[22] Filed: Jul. 14, 1993

[51] Int. Cl.$^6$ .................................. C07C 59/00
[52] U.S. Cl. ........................... 554/216; 554/169; 554/206
[58] Field of Search ................... 554/206, 169, 216

[56] References Cited

U.S. PATENT DOCUMENTS

| | | | |
|---|---|---|---|
| 2,654,767 | 10/1953 | Hunn | 260/410.9 |
| 3,634,497 | 1/1972 | Budke | 260/497 |
| 3,641,076 | 0/1972 | Booth | 260/429 |
| 3,857,895 | 12/1974 | Booth | 260/604 |
| 3,981,798 | 9/1976 | Ries et al. | 208/323 |
| 4,078,901 | 3/1978 | Sung et al. | 44/64 |
| 4,193,771 | 3/1980 | Sharp et al. | 48/197 |
| 4,334,893 | 6/1982 | Lang | 48/202 |
| 4,421,640 | 12/1983 | Watson et al. | 208/326 |
| 4,608,202 | 8/1986 | Lepper et al. | 260/410.9 |
| 4,935,550 | 6/1990 | Miller et al. | 568/454 |
| 4,950,629 | 8/1990 | Bodurow | 502/24 |

FOREIGN PATENT DOCUMENTS

| | | |
|---|---|---|
| 543906 | 11/1981 | Australia . |
| 0127104 | 12/1984 | European Pat. Off. . |
| 0131991 | 1/1985 | European Pat. Off. . |
| 0249463 | 12/1987 | European Pat. Off. . |
| 3707563 | 9/1988 | Germany . |
| 84/5401 | 2/1986 | South Africa . |
| 2158457A | 11/1985 | United Kingdom . |
| WO91/15452 | 10/1991 | WIPO . |
| WO93/09212 | 5/1993 | WIPO . |
| WO94/17027 | 8/1994 | WIPO . |

OTHER PUBLICATIONS

Feng, Y. et al., "Chemical Composition of Tall Oil-Based Cetane Enhancer for Diesel Fuels," *Proceedings of First Biomass Conference of the Americas: Energy, Environment Agriculture, and Industry*, vol. II, pp. 863–875 (1993).

Freedman, B. et al., "Fatty Esters from Vegetable Oils for Use as a Diesel Fuel," *Vegetable Oil Fuels, Proceedings of the International Conference on Plant and Vegetable Oils*, pp. 117–122 (1982).

Freedman, B. et al., "Variables Affecting the Yields of Fatty Esters from Transesterified Oils," *J. Am. Oil Chem. Soc.*, 61:1638–1643 (1984).

Gauglitz, E. J. et al., "The Preparation of Alkyl Esters from Highly Unsaturated Triglycerides", *J. Am. Oil Chem. Soc.* 40:197–198 (1963).

Harrington, K. J. et al., "A Comparison of Conventional and in situ Methods of Transesterification of Seed Oil from a Series of Sunflower Cultivars," *J. Am. Oil Chem. Soc.*, 62:1009–1013 (1985).

Hasset, D. J. "Chemically Modified Vegetable Oil as a Diesel Fuel," *Vegetable Oil as Diesel Fuel Seminar III*, pp. 72–77 (1983).

Hasset, D. J. et al., "The Design, Construction, and Operation of a Plant to Produce Vegetable Oil Methyl Esters for Use as a Diesel Fuel," *ND Mining & Mineral Resources Research Institute, Energy and Mineral Research Center* (1988).

(List continued on next page.)

Primary Examiner—José G. Dees
Assistant Examiner—Deborah D. Carr
Attorney, Agent, or Firm—Christensen, O'Connor, Johnson & Kindness

[57] ABSTRACT

Triglycerides, such as vegetable oils and animal fats, are esterified with alcohols to produce alcohol esters which can be used as alternative fuel sources. By-products of the transesterification reaction are stripped from the effluent of the transesterification reactor using a recovery alcohol that can be an isolated by-product of the transesterification reaction.

29 Claims, 11 Drawing Sheets

OTHER PUBLICATIONS

Holmberg, W. C. et al., "National Soydiesel Development Board Standards for Biodiesel," *Proceedings of First Biomass Conference of the Americas: Energy, Environment, Agriculture, and Industry*, vol. II, pp. 876–890 (1993).

Korus, R. A. et al., "Biodiesel, Alcohol Esters of Vegetable Oil: Ethyl Ester of Rape Oil," *18th Annual Conference of the Solar Energy Society of Canada*, pp. 224–228 (1992).

Korus, R. A. et al., "Transesterification Process to Manufacture Ethyl Ester of Rape Oil," *Proceedings of First Biomass Conference of the Americas: Energy, Environment, Agriculture and Industry*, vol. 88, pp. 815–826 (1993).

Kusy, P. F., "Transesterification of Vegetable Oils for Fuels," Vegetable Oil Fuels, Proceedings of the International Conference on Plant Vegetable Oil Fuels, ASAE 4(82), 127–137 (1982).

Lago, R. C. A. et al., "Extraction and Transesterification of Vegetable Oils with Ethanol," *Oleagineaux*, 40(3):147–154 (1985).

Nelson, R. G. et al., "Energetic and Economic Feasibility Associated with the Production, Processing and Conversion of Beef Tallow to Diesel Fuel," *Proceedings of First Biomass Conference of the Americas: Energy, Environment, Agriculture, and Industry*, vol. II, pp. 848–862 (1993).

Nye, M. J. et al., "Esters from Rapeseed Oil as Diesel Fuel," *Proceedings from the Vegetable Oil as Diesel Fuel Seminar III*, pp. 78–83 (1983).

Nye, M. J. et al., "Conversion of Used Frying Oil to Diesel Fuel by Transesterification: Preliminary Test," *J. Am. Oil Chem. Soc.*, 60:1598–1601 (1983).

Peterson, C. L. et al., "Batch Type Transesterification Process for Winter Rape Oil," *ASAE*, 7(6),711–716 (1991).

Peterson, C. L. et al., "Use of Vegetable Oil as a Fuel in Time of Emergency", University of Idaho, College of Agriculture Misc. Series No. 111 (1988).

Peterson, C. L., "Vegetable Oil as a Diesel Fuel—Status and Research Priorities," i ASAE, 29(5):1413–1422 (1986).

Peterson, G. R. et al., "Rapeseed Oil Trnasesterification by Heterogeneous Catalysis," *J. Am. Oil Chem. Soc.*, 61:1593–1597 (1984).

duPlessis, L. M., et al., "Methods of Preparing and Purifying Methyl and Ethyl Fatty Acid Esters from Sunflowerseed Oil," *Proceedings from the 2nd National Conference on Fuels from Crops*, SAE–Australasia (1983).

Pudel, F. et al., "Processing Waste Fats into a Fuel Oil Substitute," *Proceedings of First Biomass Conference of the Americas: Energy, Environment, Agriculture, and Industry*, vol. II, pp. 928–930 (1993).

Reed, T. B., "An Overview of the Current Status of Biodiesel," *Proceedings of First Biomass Conference of the Americas: Energy, Environment, Agriculture, and Industry*, vol. II, pp. 797–813 (1993).

Stern, R. et al., "Preparation of Methyl and Ethyl Esters from Crude Vegetable Oils and Soapstock," *Proceedings of the World Conference on Emergency Technology* (1985).

Treybal, Robert E., *Liquid Extraction*, pp. 346–398 (1951).

Weber, J. A. et al., "Cost Implications of Feedstock Combinations for Community Sized Biodiesel Production," *Proceedings of First Biomass Conference of the Americas: Energy, Environment, Agriculture, and Industry*, vol. II, pp. 910–915 (1993).

"Vegetable Oils: Form Table to Gas Tank," *Chemical Engineering*, pp. 35–39 (1993).

5,424,467

METHOD FOR PURIFYING ALCOHOL ESTERS

FIELD OF THE INVENTION

The present invention relates to the transesterification reaction between alcohols and triglycerides such as vegetable oils or animal fats to produce alcohol esters of the triglycerides.

BACKGROUND OF THE INVENTION

Alcohol esters of triglycerides have been shown to be desirable alternatives for petroleum diesel fuel. One method for producing alcohol esters of vegetable oils involves a transesterification reaction between a vegetable oil and an alcohol. The transesterification reaction is preferably carried out in an excess of the theoretical, stoichiometric quantity of alcohol and a catalyst. The products from the reaction are: (1) an alcohol ester of vegetable oil; (2) by-product alcohol, such as glycerin; (3) unreacted excess alcohol; and (4) residual and spent catalyst. The by-product alcohol is insoluble in the alcohol ester. Accordingly, upon completion of the reaction in a reactor vessel, the reaction products separate into two phases: an ester rich phase and a by-product alcohol rich phase. The unreacted excess alcohol and residual and spent catalyst are distributed between the ester and by-product alcohol rich phases.

An existing process for the production of a methyl ester of rapeseed oil involves reacting excess methyl alcohol with the rapeseed oil. The reaction products are allowed to separate into the ester phase and alcohol phase. The two phases are then separated and then the ester rich phase is washed with water to remove unreacted methyl alcohol, residual catalyst, and spent catalyst. This water washing step requires large volumes of water, the handling of which contributes to the size of the equipment and the expense of operating such equipment. Also, the wash water including the extracted methyl alcohol and the residual and spent catalyst is disposed of without further treatment resulting in a loss of these materials. The wasting of these materials is an economic loss and an environmental disposal problem.

Waste oils and animal fats, for example from meat packing plants, and food processing plants frying oil waste, are also potential sources of raw material for the transesterification reaction to produce alcohol esters. Plentiful sources of these starting materials exist. The purified alcohol esters can be used as fuel alternatives and in other high value end products such as detergent surfactants, herbicides, pesticides diluents, sticking agents, or lubricating additives for hydraulic and transmission fluids.

In view of the increasing interests in alternative fuel sources and other uses of purified alcohol esters, there exists a need for a more economical and environmentally sound process for producing alcohol esters of triglycerides.

SUMMARY OF THE INVENTION

The present invention provides an economical and environmentally sound process for producing purified alcohol esters of triglycerides, from sources such as vegetable oils, fish oil, animal fat, waste oil/fat mixtures, or possibly synthetic sources. The present invention relies upon a by-product alcohol, such as glycerin, or a recovery alcohol to purify the alcohol ester to a degree that alcohol esters produced in accordance with the present invention do not require water washing as prior processes require. In accordance with the present invention, impurities removed by the by-product alcohol or recovery alcohol can subsequently be recovered so that the impurities and the alcohol can be reused. Accordingly, the present invention reduces the economic loss of lost materials and the environmental problem of disposing of the wash water.

In one aspect, the present invention is a method for purification of an alcohol ester produced by a transesterification reaction between an alcohol and a triglyceride. The transesterification reaction occurs in the presence of a catalyst. The alcohol ester is purified by separating a first phase including the alcohol ester, unreacted alcohol, and catalyst from a second phase that includes a by-product alcohol, such as glycerin, unreacted alcohol, and catalyst. The second phase is treated to separate the byproduct alcohol from the unreacted alcohol and catalyst. The first phase is treated with the separated by-product alcohol to separate unreacted alcohol and catalyst from the alcohol ester. The removal of unreacted alcohol and catalyst and other impurities is complete enough that the alcohol ester does not require subsequent water washing. Since, in accordance with preferred embodiments of this aspect of the present invention, the separated by-product alcohol used to separate the unreacted alcohol and catalyst from the alcohol ester can be retreated for reuse, the disposal problems of prior processes described above are avoided.

In another aspect of the present invention, a recovery alcohol, such as glycerin, from a source other than the by-product alcohol from the transesterification reaction can be used in treating the first phase to separate the unreacted alcohol and catalyst from the alcohol ester.

In another aspect, the present invention relates to a method for recovering the by-products of the transesterification reaction between the alcohol and the triglyceride in the presence of a catalyst. The method involves the steps of separating a first phase including the alcohol ester, first phase unreacted alcohol, and first phase catalyst from a second phase including a by-product alcohol, second phase unreacted alcohol, and second phase catalyst. The second phase is treated to separate the second phase unreacted alcohol from the by-product alcohol and the second phase catalyst. The by-product alcohol and the second phase catalyst are then separated. The first phase is treated with the recovered by-product alcohol in order to separate the first phase unreacted alcohol and the first phase catalyst from the alcohol ester. This provides a mixture of the by-product alcohol, first phase unreacted alcohol, and the first phase catalyst. The mixture of the by-product alcohol, first phase unreacted alcohol and first phase catalyst can be combined with the second phase after it is separated from the first phase but before it is treated to separate the second phase unreacted alcohol from the by-product alcohol and the second phase catalyst. Alternatively, the mixture of the by-product alcohol, first phase unreacted alcohol and the first phase catalyst is not combined with the second phase as described above. In either case, the individual streams or the combined mixture is then separated into streams of by-product alcohol, first and second phase unreacted alcohol, and first and second phase catalyst. The by-product alcohol, first and second phase unreacted alcohol, and first and second phase catalyst are then recovered.

In a preferred embodiment, a portion of the by-product alcohol can be recycled. Since unspent catalyst is contained in the by-product alcohol, the recycle of the by-product alcohol also recycles unspent catalyst, which reduces the amount of fresh catalyst required.

The by-product alcohol rich phase also includes mono- or di-glyceride by-products that are essentially insoluble in the ester product. The mono- and di-glyceride by-products result from incomplete esterification of the triglyceride. In another preferred embodiment, the yield of alcohol ester can be increased and partial purification of the by-product alcohol can be achieved by using a secondary reactor to convert mono- and di-glycerides by-products into more alcohol ester and by-product alcohol. By treating the by-product alcohol with additional excess alcohol and/or heating, the mono- and di-glycerides can be converted to alcohol ester and by-product alcohol. Usage of a secondary reactor increases the yield of both valuable products and reduces the amount of residue that must be disposed of.

Brief Description of the Drawings

The foregoing aspects and many of the attendant advantages of this invention will become more readily appreciated as the same becomes better understood by reference to the following detailed description, when taken in conjunction with the accompanying drawings, wherein.

Detailed Description of the Preferred Embodiment

A more detailed description of the present invention is presented by reference to the previously cited FIGS. 1-17 which are provided for explanatory purposes only and are not meant to define or limit the scope of the invention.

Esters undergo reaction with alcohols to give a new ester and a new alcohol. This reaction is catalyzed by either acid or base and is called transesterification. Triglycerides, such as vegetable oils or animal fats, and alcohols can be transesterified to produce purified esters. In the following description, the present invention will be described in the context of transesterification of rapeseed oil with methyl alcohol or ethyl alcohol to produce purified esters. It should be understood that the following description refers to the specific triglyceride, vegetable oil; however, the reference to the vegetable oil is for clarity only and the present invention applies to triglycerides from sources other than vegetable oil. Furthermore, other types of alcohols can be employed to provide purified esters in accordance with the present invention.

Figure 1:
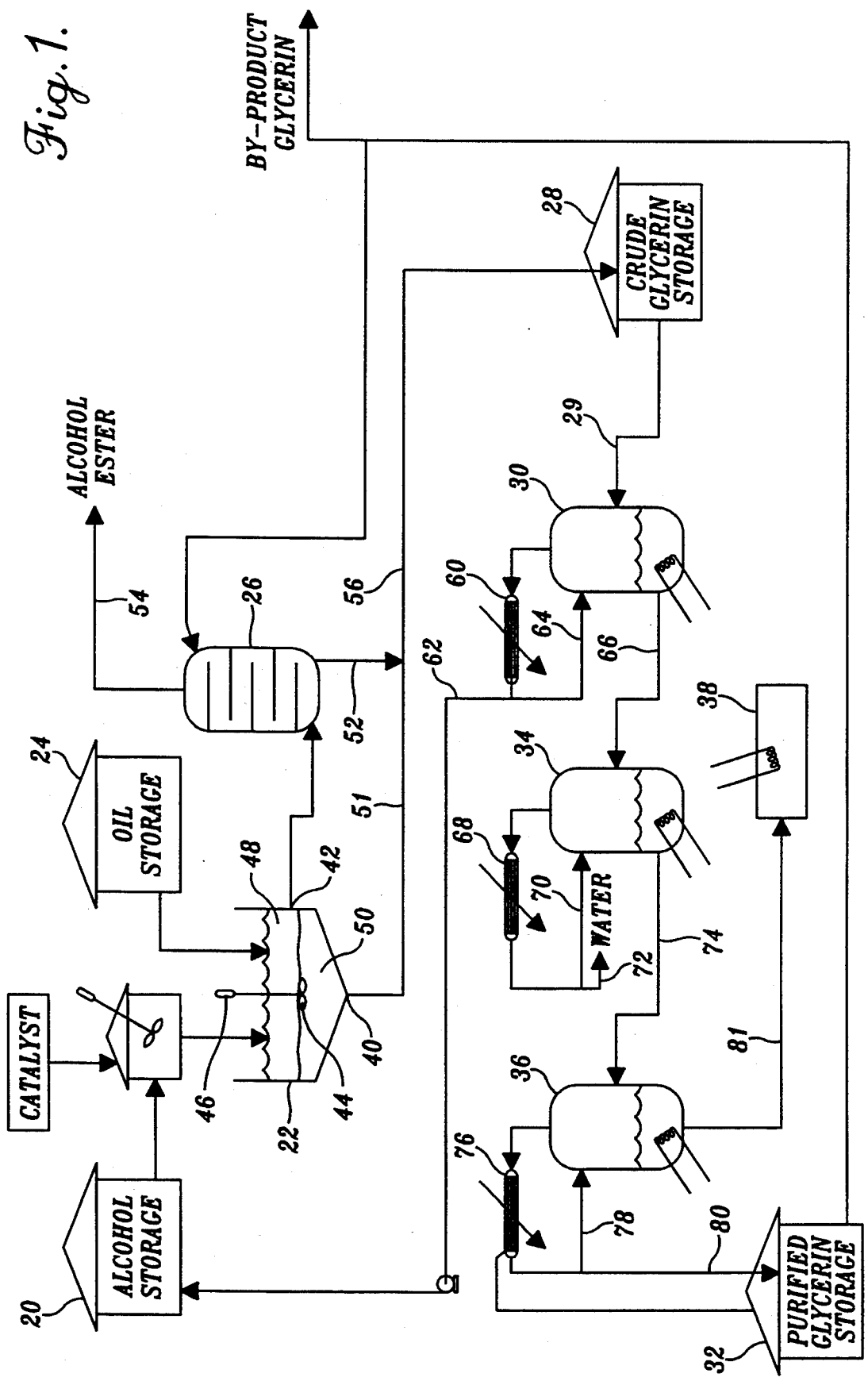
FIG. 1 is a schematic flow chart for a method for producing alcohol esters of triglycerides in accordance with the present invention.

Referring to FIG. 1, the basic flow of a process formed in accordance with the present invention is illustrated. Methyl alcohol from storage tank 20 is mixed with catalyst and introduced into transesterification reactor 22 in an amount in excess of the theoretical stoichiometric amount. A triglyceride, such as rapeseed oil, from oil storage tank 24 is also introduced into transesterification reactor 22 with mixing. After the reaction has proceeded, a first phase 48 containing raw ester, spent catalyst, unspent catalyst, and unreacted alcohol is withdrawn from the upper portion of reactor and delivered to liquid extraction system 26. From the bottom of transesterification reactor 22 is drawn a second phase 50 that includes by-product glycerin, unreacted alcohol, unspent catalyst, and spent catalyst. For purposes of simplicity, the term "catalyst" as used hereinafter will refer to residual and spent catalyst unless otherwise indicated. First phase 48 is subjected to a liquid extraction in liquid extraction system 26 to separate unreacted alcohol and catalyst from the raw ester. In the illustrated embodiment, glycerin is used as the solvent to extract the unreacted alcohol and catalyst from the raw ester of the first phase. Glycerin is insoluble in the ester of the first phase yet has a high solubility with respect to the unreacted alcohol and catalyst. Accordingly, the glycerin extracts the unreacted alcohol and catalyst from the raw ester of the first phase. Glycerin is preferred as a solvent for the extraction since it is a natural by-product of the transesterification reaction. Second phase 50 and the raffinate in stream 52 from extraction system 26 which includes the solvent glycerin, unreacted alcohol and catalyst are delivered to glycerin storage tank 28. In the illustrated embodiment second phase 50 in stream 51 and raffinate in stream 52 are combined before delivery to storage tank 28, but this is not required. Streams 51 and 52 can be delivered separately to storage tank 28 or they can be delivered to separate storage tanks (not shown) for further processing as described below. In the illustrated embodiment, feed stream 29 from glycerin storage tank 28 is delivered to extractive distillation column 30 where it is distilled to separate unreacted alcohol from the glycerin and catalyst. The vapors comprising unreacted alcohol from the extractive distillation are condensed in condenser 60 and delivered via stream 62 to alcohol storage tank 20. Bottoms from extractive distillation column 30 in stream 66 are delivered to dewatering column 34 where residual water is vaporized. The vaporized water is condensed and collected in condenser 68. The bottoms from dewatering column 34 are delivered via stream 74 to vacuum distillation column 36 where the glycerin is vaporized and separated from the catalyst. The vaporized glycerin is condensed in condenser 76 and delivered to purified glycerin storage tank 32 for holding and subsequent use either as a by-product or as a solvent for liquid extraction system 26. The bottoms of vacuum distillation column 36 that comprise catalyst and residual organic materials can be delivered to heat recovery furnace 38 where they are combusted to produce ash and flue gas.

In an alternative embodiment, partial catalyst recycle is accomplished by recirculating a portion of the glycerin from various locations in the process described above with reference to FIG. 1. For example, recycling a part of stream 51, 52, or 56 or any other catalyst containing stream will reduce the amount of fresh catalyst that is required for the reaction. Another possible source of unspent catalyst is stream 81 from the bottom of vacuum distillation unit 36. A significant amount of unspent catalyst is contained in the second phase or glycerin phase and, accordingly, recycling part of the glycerin also recycles the catalyst, which reduces the amount of fresh catalyst required. The volume of recycle will depend upon the specific system employed and can be readily determined using conventional chemical engineering techniques.

As can be seen from the flowchart, the present invention preferably uses a recycle stream of glycerin that is used as a solvent in liquid extraction system 26 wherein high purity ester is separated from unreacted alcohol and catalyst. A more detailed description of the feedstocks and various process streams and equipment is provided below.

Vegetable oils, animal fats, fish oils and the like that are useful as feedstock for the transesterification reaction include those oils that include triglycerides which can be transesterified into alcohol esters. Specific types of vegetable oils include rapeseed oil, sunflower oil, safflower oil and the like.

The alcohol feedstock can be selected from organic alcohols that undergo an alcoholysis substitution exchange reaction with the triglyceride to produce glycerin and an alcohol ester. Specific examples of suitable alcohols include methyl alcohol, ethyl alcohol, propyl alcohol, butyl alcohol and the like.

The transesterification reaction between the triglyceride and alcohol is catalyzed by bases such as potassium hydroxide, sodium hydroxide, sodium methoxide, potassium methoxide, sodium ethoxide and the like. The transesterification reaction can also be catalyzed by acids such as sulfuric acid.

The particular and preferred conditions for carrying out the transesterification reaction are described in Peterson, C. L., Feldman, M., Korus, R., and Auld, D. L. (1991), "Batch Type Transesterification Process for Winter Rape Oils" *Applied Engineering in Agriculture,* 7(6) pp. 711–716 and "Process Development of Rapeseed Oil Ethyl Ester as a Diesel Fuel Substitute" M.S. Thesis by Narendra Bam, University of Idaho, July, 1991. As noted above, in order to obtain yields in excess of 95% and complete conversion of triglycerides, an excess of the alcohol is employed. Various excess alcohol amounts can be used in combination with different catalysts, catalyst amounts and reactor temperatures. For example, in accordance with the present invention, a 100% excess of alcohol based on the theoretical stoichiometric amount of alcohol can be used at room temperature with 1% potassium hydroxide. When excess amounts of alcohol are used, in accordance with the present invention, phase separation of the ester phase and alcohol phase occurs after the transesterification reaction is completed. If sufficient excess alcohol is not employed, the addition of additional alcohol may be required to initiate the phase separation. Requiring the addition of alcohol after the transesterification is complete will result in larger equipment sizes being required to handle the increased volume.

Yields and conversions in excess of 99% have been reported in literature; however, these reported yields are based on the disappearance of the triglyceride rather than the appearance of ester. Applicants have observed that there is a partial conversion of the triglycerides to mono- or di-glycerides, accordingly the reporting of the literature of conversions of yields in excess of 99% based on the disappearance of the triglyceride is not necessarily a clear representation of the amount of ester that is produced. In other words, a reported 99% conversion of triglyceride may not necessarily translate into a yield of alcohol ester that would be equal to complete conversion of 99% of the triglyceride to ester.

Continuing to refer to FIG. 1, the individual unit operations of a method for producing alcohol esters of vegetable oils in accordance with the present invention will be described in more detail. The following detailed description will be in the context of the transesterification of rapeseed oil with methyl alcohol catalyzed by potassium hydroxide. It should be understood that the description is applicable to other vegetable oils or animal fats, alcohols and catalysts.

The transesterification reaction between the alcohol and vegetable oil is carried out in transesterification reaction vessel 22. To provide sufficient contact between the vegetable oil and the alcohol for the transesterification reaction to proceed, reaction vessel 22 includes an impeller 44 attached to motor 46. Motor 46 rotates impeller 44 so that it will agitate the reactor volume with just a slight amount of splashing. If necessary, reaction vessel 22 can be provided with a jacket (not shown) to heat or cool the contents. If the reaction is carried out in a batch manner, separation of the first phase and second phase can be achieved by allowing the reaction mixture to stand without agitation after the reaction is completed. In accordance with the present invention, the phase separation occurs without further treatment of the reaction mixture because an excess of alcohol is used. After the phase separation has occurred, the respective phases can be removed from reaction vessel 22 as described below. In the illustrated embodiment, in order to remove the lighter ester rich phase 48 and the heavier by-product alcohol rich phase 50, reaction vessel 22 is provided with a lower drain 40 adjacent its bottom and an upper drain 42 positioned above the interface between ester rich phase 48 and the alcohol rich phase 50. Upper drain 42 is used for removal of the first phase or ester rich phase 48 that generally comprises raw ester, unreacted alcohol, and catalyst. The second phase or alcohol rich phase 50 generally comprises unreacted alcohol, by-product glycerin and catalyst and is removed from the lower drain 40.

Alternatively, though not illustrated, when the reaction is carried out in a batch manner, alcohol rich phase can be drained from the bottom of the reaction vessel into a storage tank. The ester rich phase can be retained in the reaction vessel and extracted with glycerin in accordance with the present invention. Alternatively, after the alcohol rich phase is drained from the reaction vessel, the ester rich phase can be drained from the bottom of the reaction vessel and delivered to the liquid extraction system. As noted above, while the transesterification reaction and the extraction of the ester rich phase can be carried out on a batch manner, it is preferred that a continuous mixer reactor and a continuous settling system be employed as described below with reference to FIG. 2.

Vegetable oil and alcohol are introduced into the reaction vessel 22 from alcohol storage tank 20 and oil storage tank 24 that can be provided with pumps or be gravity feed tanks. The alcohol is introduced in a ratio ranging from about 7% to 40% by weight based on oil used. This amount provides the needed excess so that phase separation will occur after the reaction is complete. Prior to introduction of alcohol into reaction vessel 22, catalyst is mixed into the alcohol. The catalyst is used in an amount ranging from about 0.1% to 2.0% by weight based on oil used. Reaction times are dependent upon the temperature of the reaction vessel, catalyst type and amount, and excess alcohol used. Reaction times less than 60 minutes can readily be selected to obtain over 99% conversion of triglycerides when potassium hydroxide is used as catalyst and the reaction is carried out at room temperature.

Liquid extraction system 26 that separates unreacted alcohol and catalyst from the raw ester of the first phase can be of any conventional design provided that adequate contact between the first phase and the solvent is achieved so that the unreacted alcohol and catalyst are separated from the raw ester. In accordance with the present invention, the ratio of solvent to the first phase should be in a range that provides the desired separation. While solvent to ester ratios can be very small if more contact stages are used during the extraction process, there is an economic tradeoff between less extraction equipment stages and larger solvent flows. Solvent to first phase ratios ranging between about 1:1 to about 1:20 or more can achieve suitable separation. Preferably, the solvent to first phase ratio ranges between about 1:1 to about less than 1:4 so that the number of extraction stages is kept at an economically reasonable number. Suitable equipment for liquid extraction system 26 can be operated batchwise or continuously. For example, in a batch process, after the first phase and second phase are separated a quantity of first phase may be mixed with a quantity of solvent, e.g., glycerin in agitated vessel, after which the layers are settled and separated into extract and raffinate. This operation can be repeated if more than one theoretical contact stage is required to achieve the desired extraction. When the quantities of ester involved are large and several contacts are needed, continuous flow becomes more economical and is preferred. Representative types of extraction units include mixer settlers, vertical towers of various kinds that operate by gravity flow, agitated tower extractors, and centrifugal extractors. The particular configuration and design of the individual components of a liquid extraction system can be readily ascertained using conventional chemical engineering calculations and techniques. One specific configuration is described in the example that follows.

As noted above, liquid extraction system 26 provides a raffinate stream 52 comprising the solvent glycerin, unreacted alcohol and catalyst, and an extract stream 54 comprising the raw ester. As noted above, the resulting raw ester is generally of a purity that does not require the water washing required by prior processes.

In the illustrated embodiment, raffinate stream 52 from liquid extraction system 26 is combined with the alcohol rich phase 50 from transesterification reactor 22 in stream 51 for further processing to separate out the unreacted alcohol, residual water, catalyst, and glycerin. As described above, although not illustrated, a portion of streams 51, 52, or 56 can be recycled to reactor 22 for the purpose of catalyst recycle. The following describes a specific scheme for separating these components; however, it should be understood that other process sequences could be used to achieve the separation.

Continuing to refer to FIG. 1, the combined raffinate stream and alcohol rich stream 56 is delivered to storage tank 28 for accumulation prior to subsequent processing. Unreacted alcohol is separated from the glycerin, catalyst, and residual water by extractive distillation. Extractive distillation can be carried out in an extractive distillation vessel 30 wherein the unreacted alcohol is vaporized while the glycerin and water remain in liquid form and the catalyst remains in solution. The vaporized unreacted alcohol is recovered and condensed in condenser 60. A portion of the condensed unreacted alcohol is returned to storage tank 20 via stream 62 and serves as feedstock for transesterification reactor 22. A portion of the condensed recovered alcohol is recycled via stream 64 to extractive distillation vessel 30 in order to maintain the needed equilibrium. The particular conditions of the extractive distillation can be determined using conventional chemical engineering techniques and theories. The bottoms from extractive distillation vessel 30 comprise glycerin, residual water, and catalyst. The bottoms are delivered via stream 66 to dewatering column 34 where the residual water is vaporized to separate it from the glycerin and catalyst. The vaporized water is collected and condensed by condenser 68 with a portion being returned via stream 70 to dewatering column 34 as reflux and the remaining portion being disposed of via stream 72. The operating conditions for the dewatering column can be determined using known chemical engineering techniques. The bottoms from dewatering column 34 that include glycerin, organic residues, and catalyst are delivered to vacuum distillation column 36 via stream 74 where the glycerin is vaporized to separate it from the catalyst and organic residue. The vaporized glycerin is collected and then condensed in condenser 76. A portion of the condensed glycerin is returned to vacuum distillation column 36 as reflux via stream 78 and the remaining portion in stream 80 provides by-product glycerin and a source of solvent for liquid extraction system 26 described above. The particular conditions of the vacuum distillation can be determined using conventional chemical engineering techniques.

The bottoms from vacuum distillation column 36 are collected and delivered to heat recovery furnace 38, where they are combusted to produce flue gas and ash. The ash contains spent and unspent catalyst residue. The heat generated by the combustion of the catalyst is recovered for use in other unit operations. Since the bottoms from vacuum distillation column 36 include spent catalyst and unspent catalyst, optionally a portion of the bottoms from vacuum distillation column 36 can be collected and delivered to reactor vessel 22, thus recycling some of the unspent catalyst.

In accordance with the present invention, the use of glycerin in the liquid extraction provides an extract stream of ester that is greater than about 99% pure. Preferably, the ester contains less than about 100 parts per million of impurities such as residual spent or unspent catalyst. Ester of this purity generally does not need to be washed to remove impurities prior to further use as an alternative fuel. By circumventing the water washing step required by the prior processes, the creation of a waste water stream and the waste of alcohol and unspent catalyst is reduced. It should be understood that the use of glycerin as a solvent in the liquid extraction process can be designed to produce an ester stream of almost any desired purity specification. For example, using amounts of glycerin solvent described above will provide an ester that is greater than 99% pure; however, if desired, the amount of glycerin solvent used and/or the number of stages used in the extraction system can be reduced to produce ester products of lower purity. Conversely, increasing the amount of glycerin solvent used and increasing the number of stages in the extraction system will result in an even higher purity ester product.

As described above, the conversion of triglycerides to alcohol esters in the transesterification reaction can be less than complete. Accordingly, mono- and diglycerides are also by-products of the transesterification reaction. Increased yield of ester and supplemental purification of the glycerin can be achieved by subjecting the second phase or the combined second phase and raffinate from the liquid extraction system to a secondary reaction to convert the mono- and di-glycerides into more ester and glycerin. For example, the mono- and di-glycerides in the second phase can be converted into more ester by adding excess alcohol to the second phase after it is separated from the ester rich first phase. This secondary reaction can be carried out in a secondary reactor (not shown). The resulting product can be delivered to the liquid extraction where the impurities can be separated from the ester. Alternatively, the second phase can be heated after it is separated from the first phase in order to convert mono- and di-glycerides into more ester and glycerin. A combination of adding excess alcohol and heating the resulting mixture will also result in conversion of the mono- and di-glycerides into ester and glycerin. When the second phase is heated at atmospheric pressure, the maximum temperature of heating will be limited by the boiling point of the alcohol being used in the transesterification reaction. Pressurizing the vessel in which the second phase is heated would allow heating at higher temperatures and would result in even higher yields of ester and glycerin from the mono- and di-glycerides.

The example below provides a specific description of one embodiment for carrying out the transesterification of a vegetable oil using glycerin as a solvent in accordance with the present invention.

Example

Figure 2:
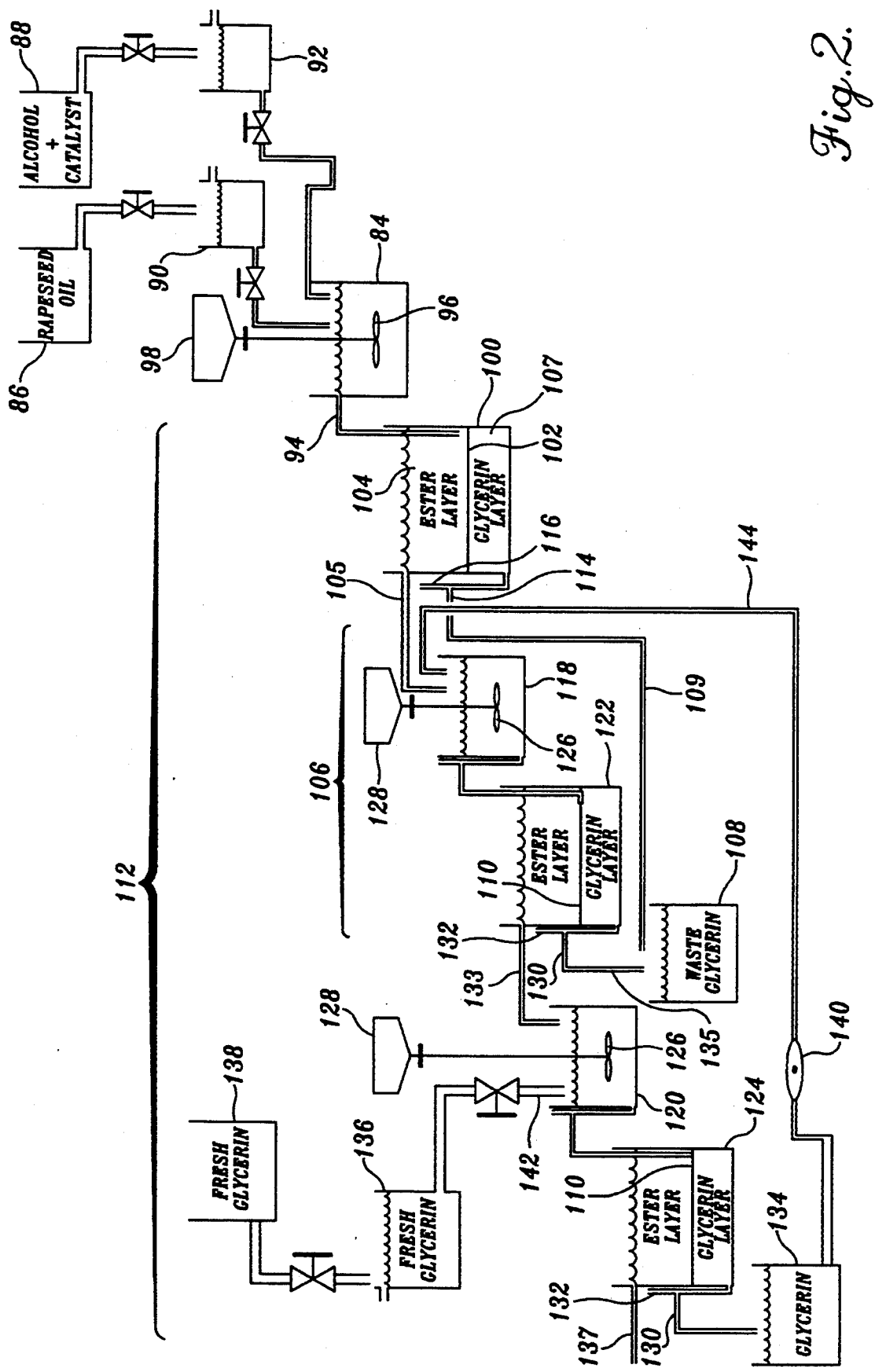
FIG. 2 is a detailed schematic drawing of the bench scale system described in the Example.
Figure 3:
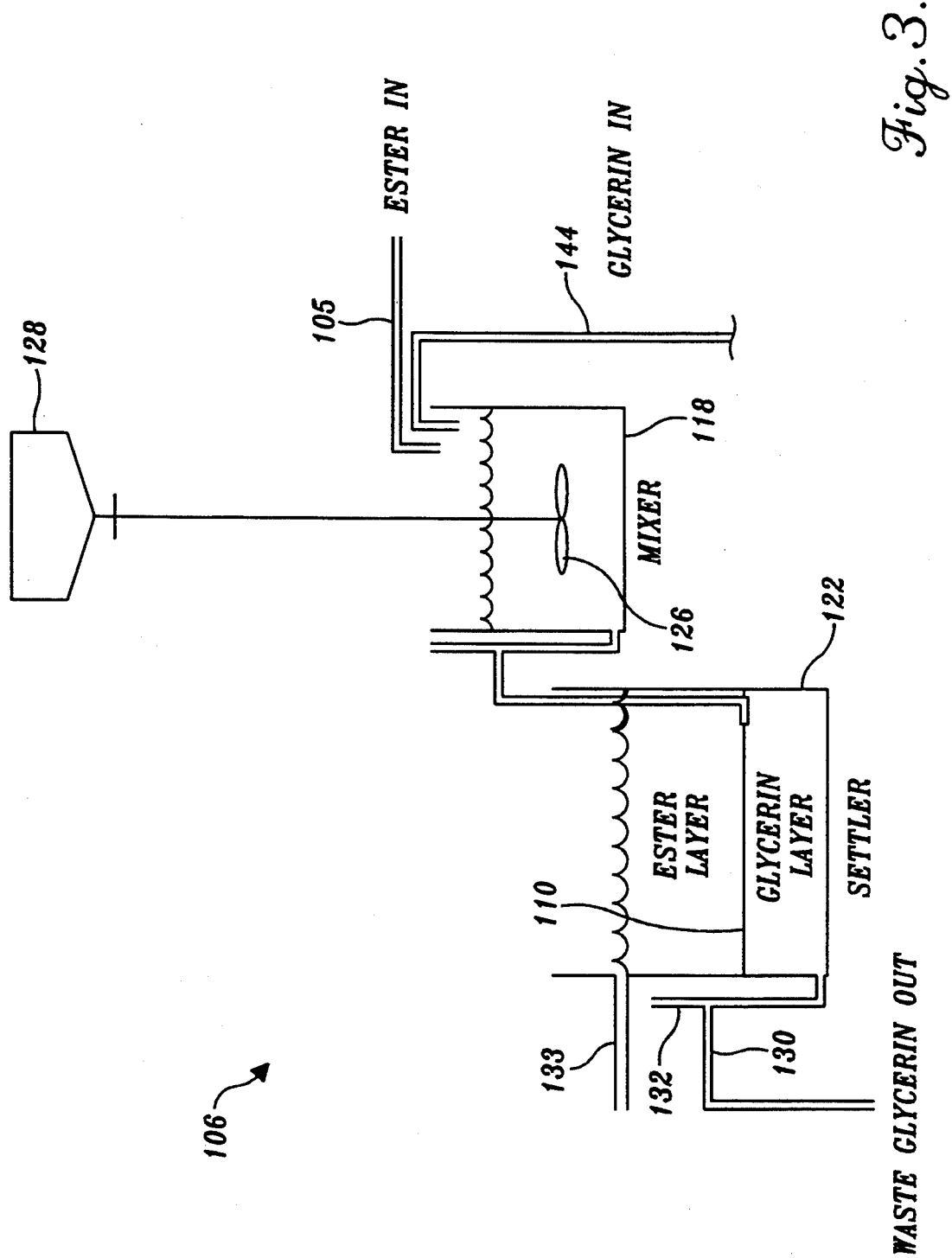
FIG. 3 is a detailed schematic of one extraction stage of FIG. 2.

A bench scale two stage mixer-settler was constructed and operated. The apparatus consisted of raw material supply vessels, a continuous reactor, and a two stage mixer-settler extractor. A flow sheet diagram of the process is shown in FIG. 2. FIG. 3 provides a detailed view of a mixer-settler section.

Referring to FIGS. 2 and 3, rapeseed oil and a mixture of potassium hydroxide catalyst in methyl alcohol were delivered to transesterification reactor 84 via tubing from gravity feed tanks 86 and 88. Two 250 milliliter beakers fitted with hose barbs at the top and bottom served as constant head tanks 90 and 92 to supply reactor 84 with a constant flow of raw material. Constant head tanks 90 and 92 were over supplied with raw material from two 1,000 milliliter beakers fitted with hose barbs at the bottom. In this way, the 250 milliliter beakers were allowed to constantly overflow, thereby keeping the liquid level in each tank and the static head constant. The rapeseed oil was transported in $\frac{1}{4}''$ inner diameter, $\frac{3}{8}''$ outer diameter Nalgene 280 ester grade polyurethane tubing. This same tubing was initially used for the alcohol-potassium hydroxide mixture, but the tubing was quickly dissolved by the mixture. Accordingly, a $\frac{1}{4}''$ inner diameter, $\frac{3}{8}''$ outer diameter Van Waters and Rogers, Inc. vinyl tubing performed satisfactorily. The rapeseed oil flow was measured in an Atheson Gas Products 604 15 centimeter dual ball rotameter calibrated using a graduated cylinder and stop watch to the oil flow rate. The alcohol mixture flow was measured in an Atheson Gas Products 601 15 centimeter dual ball rotameter calibrated to the alcohol mixture flow rate.

Transesterification reactor 84 was a 1,000 milliliter beaker fitted with a hose barb at the bottom toward the exit point. The volume in the reactor was controlled by the height of the overflow exit tube 94 and was set at approximately 500 milliliters for this experiment. The agitation of reactor 84 was accomplished by a 38 millimeter impeller 96 attached to a 5,000 RPM Bodine DC motor 98. The motor RPMs were controlled by a variac (not shown) and were set to agitate the reactor volume with just a slight amount of splashing which was approximately 1,700 RPMs.

The reactor effluent was gravity fed from reactor 84 in $\frac{1}{4}''$ inner diameter, $\frac{3}{8}''$ outer diameter Nalgene 280 ester grade polyurethane tubing and was injected into a 2,000 milliliter beaker that served as a primary settler 100 fitted with hose barbs at the top and the bottom. The feed from reactor 84 was injected at the ester glycerin interface 102 in primary settler 100. Ester phase 104 was then taken off the top of settler 100 via stream 105 and overflowed by gravity to first stage 106 of the extraction mixer-settler 112. The glycerin from primary settler 100 was taken off the bottom and passed to a waste container 108 via stream 109. The height of the glycerin-ester interface 102 in settler 100 was controlled by the height of glycerin exit tube 114 with a siphon brake 116 attached. The tubing used to transport the ester and glycerin exiting primary settler 100 was 5/16" inner diameter, 7/16" outer diameter Tygon tubing. The reason for using larger tubing was because the $\frac{1}{4}''$ hose barbs could not be attached to the beaker and the larger 5/16" barbs.

Mixer-settler extraction section 112 was composed of two mixer vessels 118 and 120 and two settler vessels 122 and 124 that made a two stage mixer-settler 112 with counter-current flow. Mixer vessels 118 and 120 were 250 milliliter beakers with hose barbs on the top to allow overflow of the mixture to the settler. The mixtures were agitated with 26 millimeter impellers 126 driven by 1,750 RPM AC Bodine motors 128. All fluids in the mixer-settler area were transported in the $\frac{1}{4}''$ inner diameter, $\frac{3}{8}''$ outer diameter Nalgene 280 ester grade polyurethane tubing.

Settlers 122 and 124 were 1,000 milliliter beakers with hose barbs attached to the bottom and at approximately the 800 milliliter mark on the beaker. The effluent from the respective mixer vessels 118 and 120 was injected approximately at the ester glycerin interfaces 110. The level of interfaces 110 was controlled by the height of the exiting glycerin tubes 130 with siphon brakes 132 just as the interface was controlled in primary settler 100. Ester from first settler 122 passed to second mixer 120 via stream 133 and the glycerin from first settler 122 went to waste container 108 via stream 135. Second settler 124 produced the final purified ester in stream 137 and the glycerin from settler 124 was collected in a surge tank 134.

Fresh glycerin was supplied to the second mixer 120 by a constant head tank 136 similar to tank 86 supplying reactor 84. The glycerin supply system was composed of a 1,000 milliliter beaker 138 feeding a 250 milliliter constant head beaker 136 fitted with hose barbs on the top and the bottom. The glycerin from the second stage effluent surge tank 134 (which was 250 milliliter beaker fitted with a hose barb on the bottom) was pumped with a Masterflex Size 14 pump 140 driven by a 1,000 RPM drive. Pump 140 was calibrated as closely as possible to meter the flow of glycerin to first mixer 118. The flow of fresh glycerin was controlled by adjusting the flow with a tube clamp so that the number of drops flowing from supply tube 142 in a certain amount of time were equal to the number of drops coming from pump tube 144. This type of control was necessary because no rotameter could accurately measure the glycerin flow due to its viscosity.

A total of five experimental runs were made with the mixer-settler described above. Three runs were made using methyl ester produced in the continuous reactor. The two other runs were made by directly feeding unwashed ethyl ester to the mixer-settler. On each run the ratio of glycerin to ester was changed in order to determine how little glycerin could be used.

Methyl Ester Runs

Three methyl ester runs were made with glycerin to ester ratios of 1:1, 1:1.5, 1:2. The ester production rates for these runs were 3.5 milliliters per minute, 5.2 milliliters per minute, and 7 milliliters per minute, respectively with the glycerin flow rates remaining constant at approximately 3.5 milliliters per minute. Each run was made sufficiently long to account for the dead time in the system so that ester produced at the start of the run would have time to pass through the system before samples were taken. The experimental run times were 12 hours, 8 hours, and 6 hours, respectively. The transesterification reaction residence times were approximately 143 minutes, 96 minutes, and 71 minutes, respectively. All of the methyl ester runs were conducted at room temperature of approximately 78° F.

Figure 4:
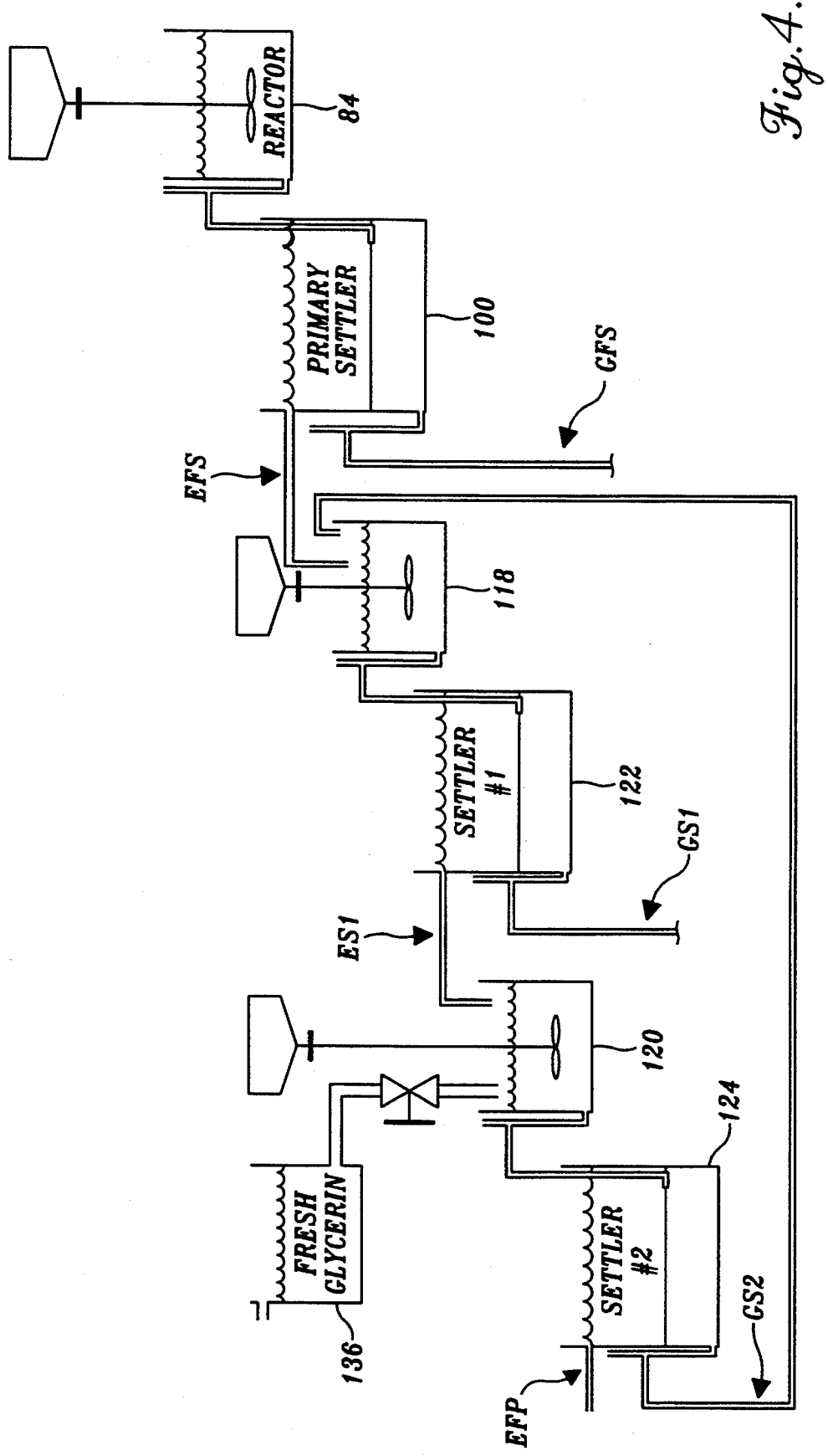
FIG. 4 is a schematic of the bench scale set up of FIG. 2 with the sampling sites identified.

Samples were taken from several places along the mixer-settler section including the feed to the extractors, the glycerin from each settler, and the alcohol ester fuel from each settler. These samples were analyzed for alcohol, ester, and glycerin content and most samples had a Plant Macro Elemental Screen (PMES) run on them. The PMES measures the phosphorous, potassium, calcium, magnesium, sulfur, and sodium content of the sample by an inductively coupled plasma analyzer. The nomenclature for the sample points is shown in FIG. 4. The results of the sample analysis are given in Table 1. The effects of the different glycerin to ester ratios are shown in FIGS. 5–11.

Figure 5:
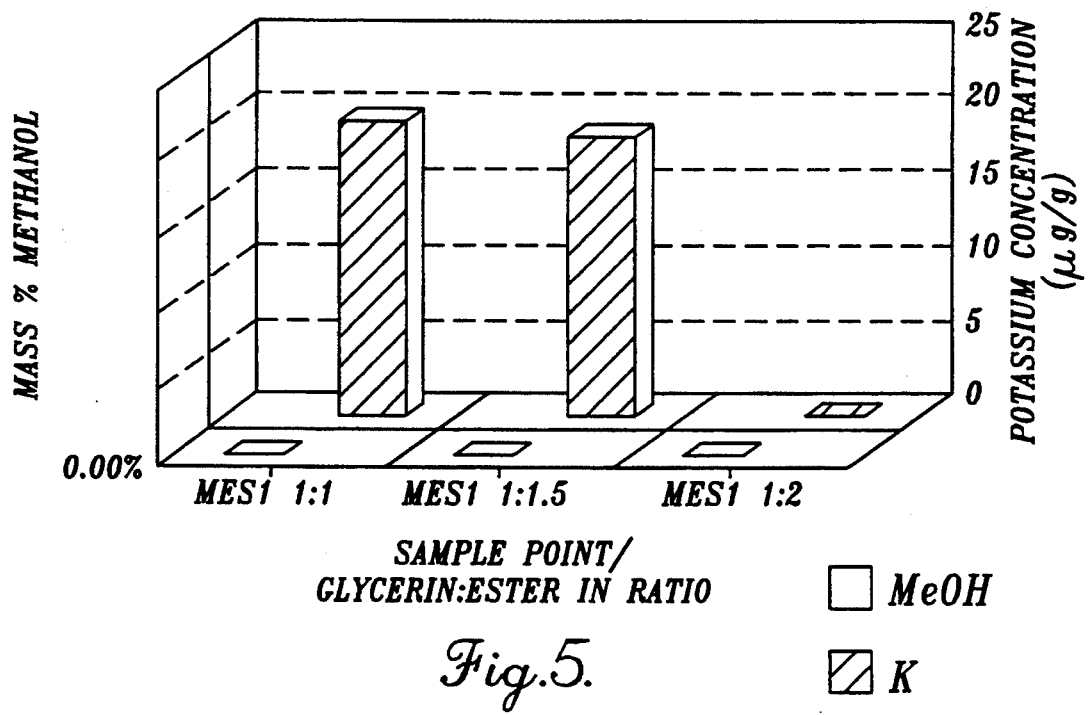
FIG. 5 is a graph illustrating the effect of ester to glycerin ratio on methyl ester from settler No. 1.

FIG. 5 shows the effect of changing the ratio of glycerin added to the incoming ester to the composition of the ester leaving first settler 122. In all cases all detectable amounts of methanol were removed in the first stage and the concentration of potassium is reduced by a factor of 10. For the 1:2 glycerin to ester ratio, no potassium was detected which may have been the result of analysis error, sampling error, or a reduction in the potassium concentration in the feed to first settler 122.

Figure 6:
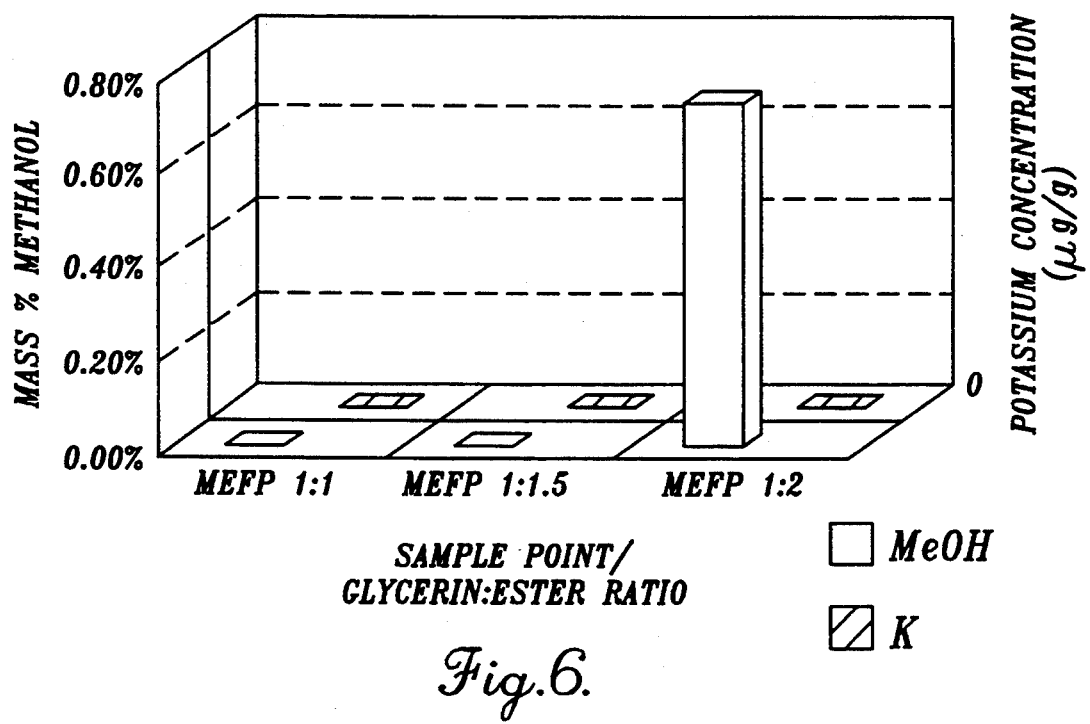
FIG. 6 is a graph illustrating the effect of ester to glycerin ratio on the final methyl ester product.

FIG. 6 is similar to FIG. 5 except that the ester is from second settler 124 where the final ester product is being analyzed. Here all concentrations have been reduced to below the detectable levels except for methanol being detected in the sample with a 1:2 ratio. Since the ester from first settler 122 for this ratio did not contain any methanol, this sample probably represents a concentration resulting from a temporary fluctuation in methanol concentration in the initial reactor and may not be truly representative of the steady state concentration.

Figure 7:
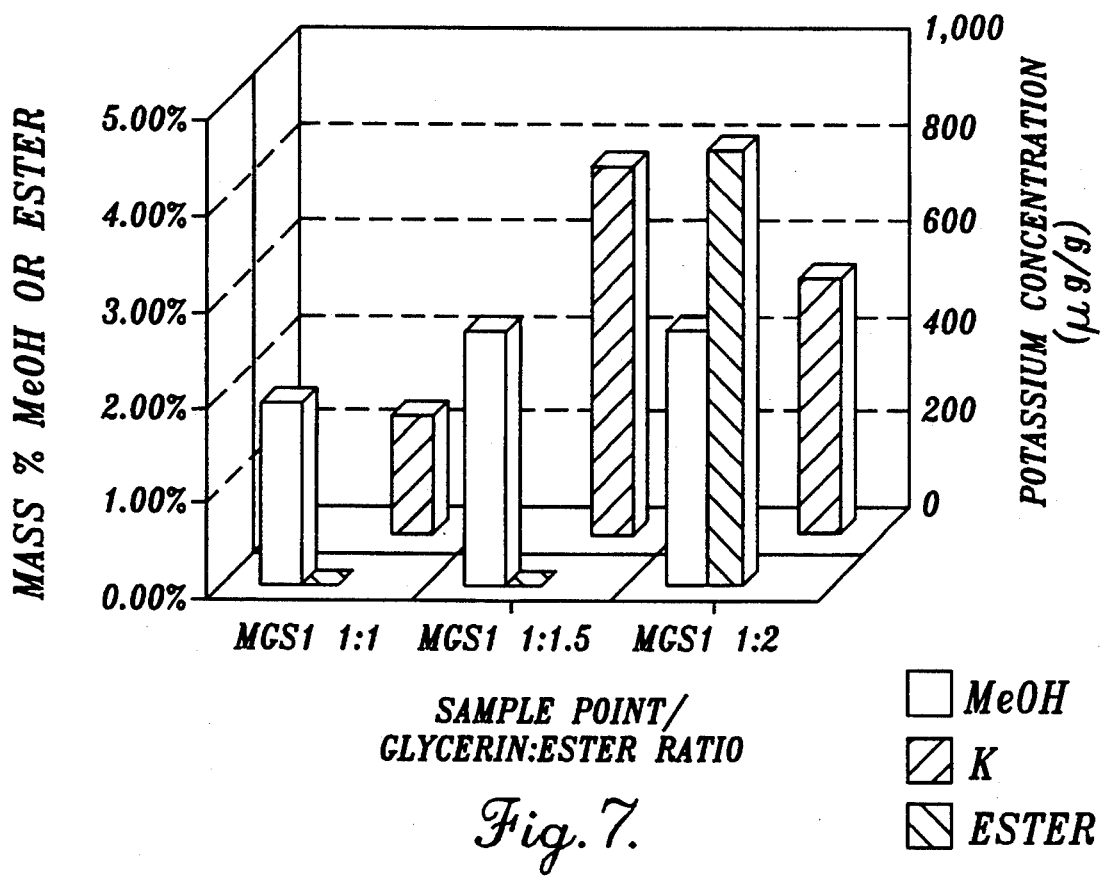
FIG. 7 is a graph illustrating the effect of ester to glycerin ratio on glycerin from settler No. 1.
Figure 8:
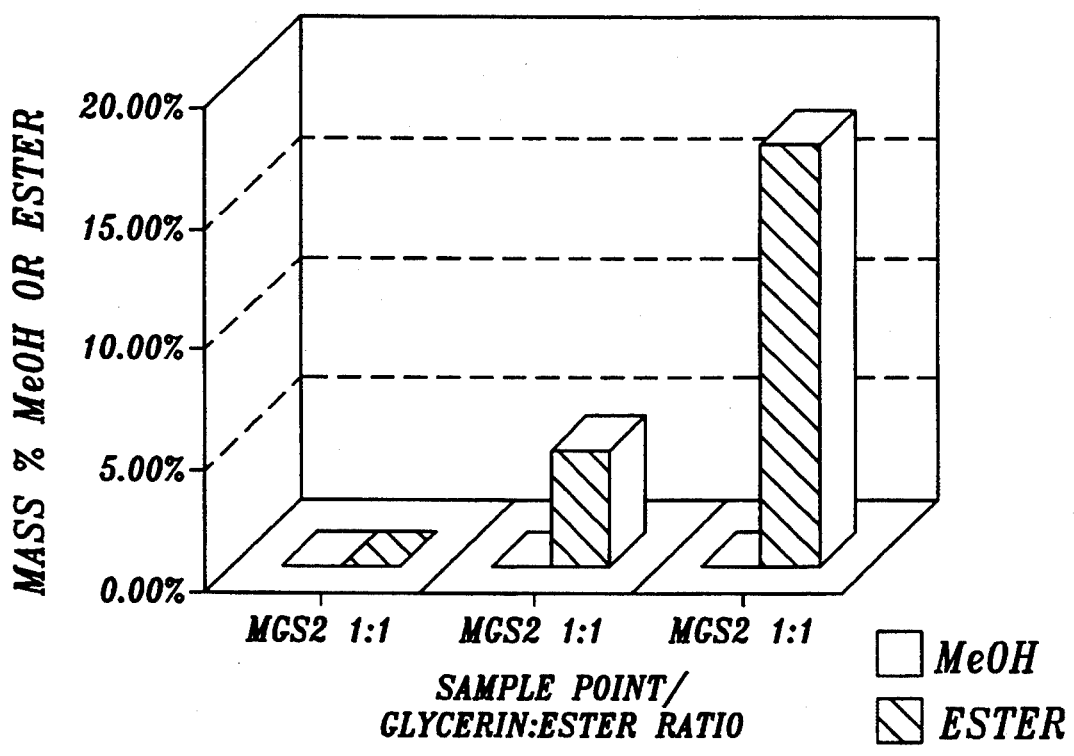
FIG. 8 is a graph illustrating the effect of ester to glycerin ratio on glycerin from settler No. 2.

FIG. 7 shows the concentrations of the glycerin from first settler 122. This FIGURE shows that the glycerin is extracting the methanol and the potassium from the ester. It can also be seen that as the amount of glycerin added per amount of ester decreases, some carryover of the ester into the glycerin is observed. FIG. 8 also supports this observation (note that the glycerin from second settler 124 was not analyzed for potassium). One possible explanation would be that the settling time was not long enough to allow for a complete phase separation. Entrainment effects may also be a possible cause because of the extreme viscosity of glycerin.

Figure 9:
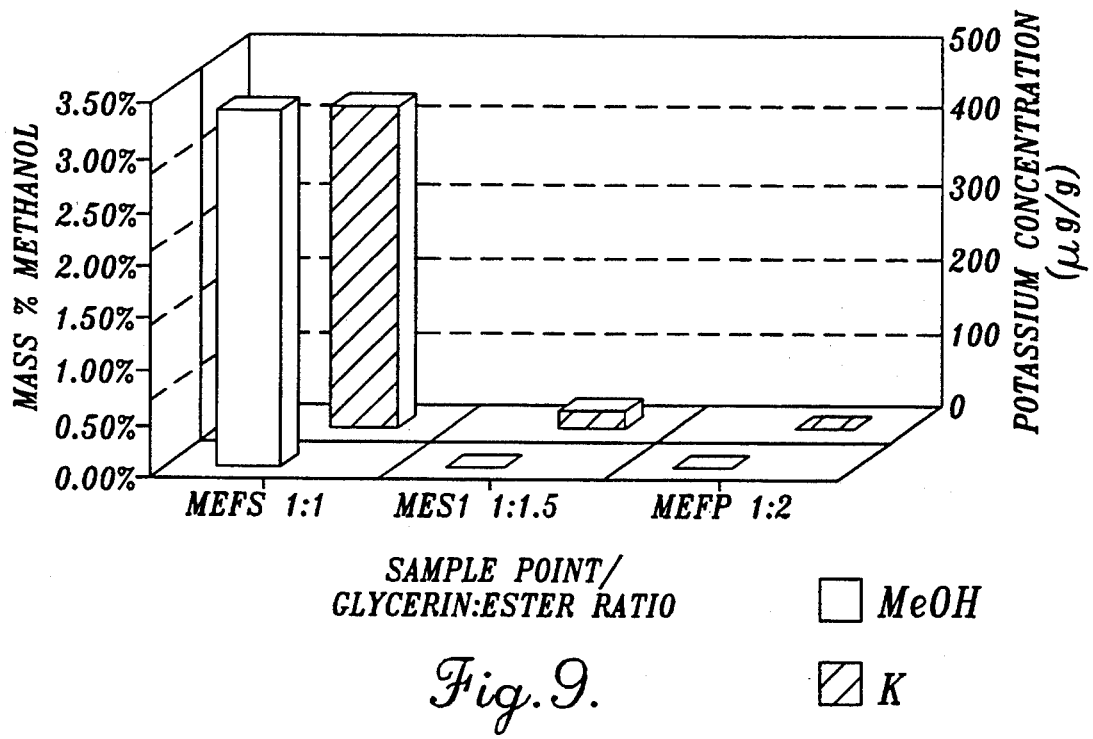
FIG. 9 is a graph illustrating the concentration profile for a 1:1 glycerin to ester ratio.
Figure 10:
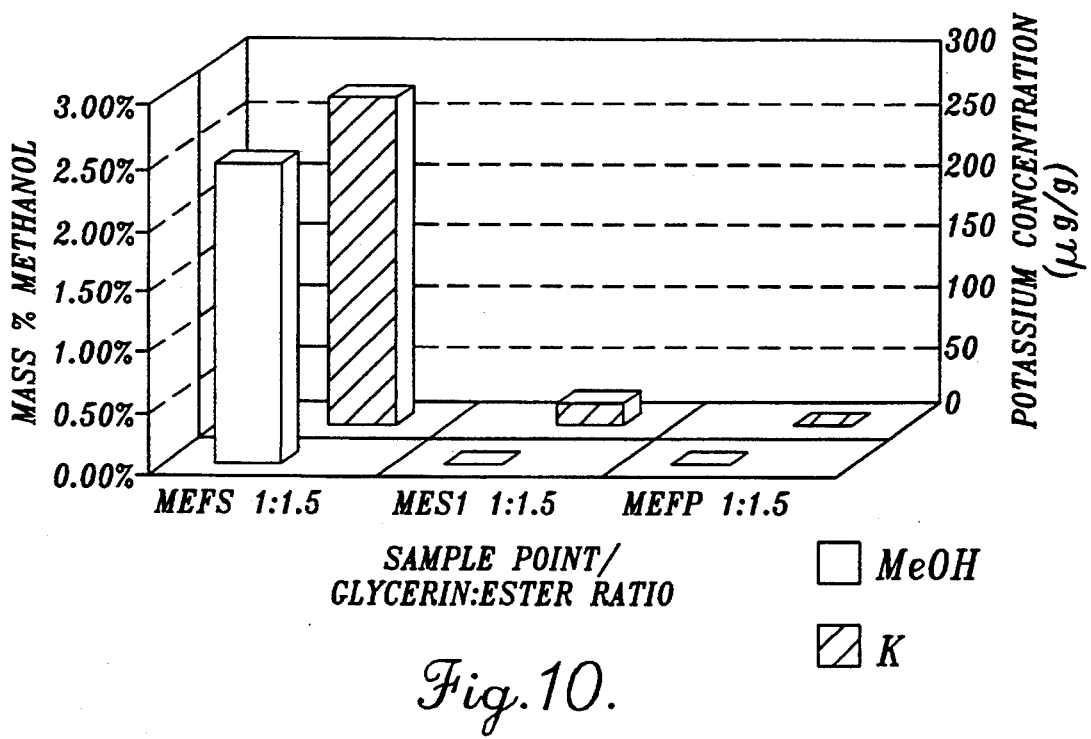
FIG. 10 is a graph illustrating the concentration profile for a 1:1.5 glycerin to ester ratio.
Figure 11:
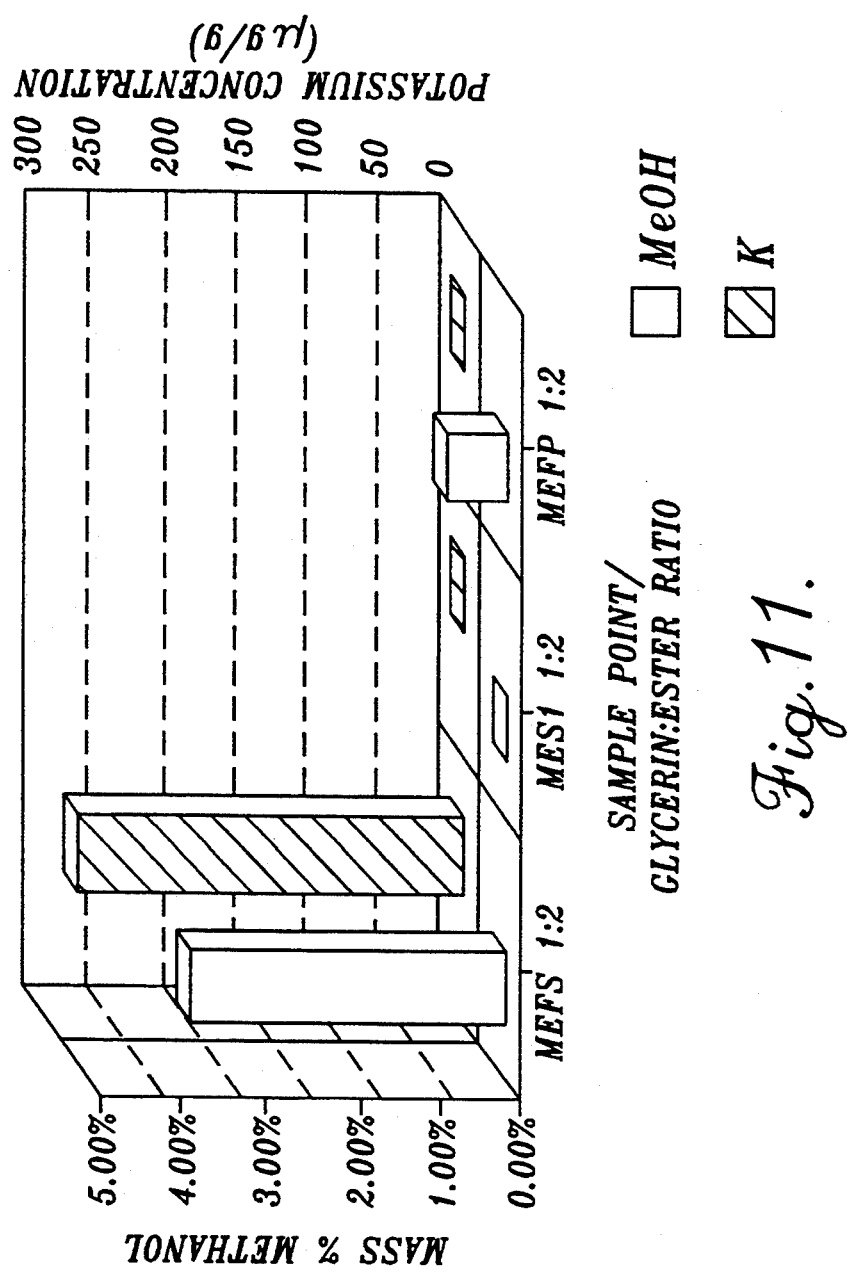
FIG. 11 is a graph illustrating the concentration profile for a 1:2 glycerin to ester ratio.

In FIGS. 9–11, the change in ester concentration from the feed to first settler 122 to second settler 124 is shown. In all cases a massive reduction in methanol and potassium is seen from the feed stock to the ester effluent from the first stage and with the second stage making little contribution. These FIGURES illustrate the effectiveness of the glycerin extraction carried out in accordance with the present invention and suggest that one stage could be eliminated, or the ratio to glycerin to ester could be further reduced.

Ethyl Ester Runs

Two ethyl ester runs were made with glycerin to ester ratios of 1:1 and 1:2. The ester feed rates for these runs were 3.5 milliliters per minute and 7 milliliters per minute, respectively with the glycerin flow rates remaining constant at approximately 3.5 milliliters per minute. Each run was made sufficiently long to account for the dead time in the system so that ester fed to the first mixer 118 at the start of the run would have time to pass through the system before samples were taken. The experimental run times were both four hours. All the ethyl ester runs were conducted at room temperature of approximately 78° F. using unwashed ethyl ester made previously in a 200-gallon batch test.

Samples were taken from the same key places along the mixer-settler section as the methyl ester run samples. These samples were also analyzed for alcohol, ester, and glycerin content as well as having a PMES run on them. The nomenclature for the sample points is analogous to the nomenclature used on the methyl ester runs with the exception of using an E to indicate ethyl ester instead of the M for methyl ester. The results of the sample analyses are given in Table 2. The effect of the different glycerin to ester ratios are shown in FIGS. 12–17.

Figure 12:
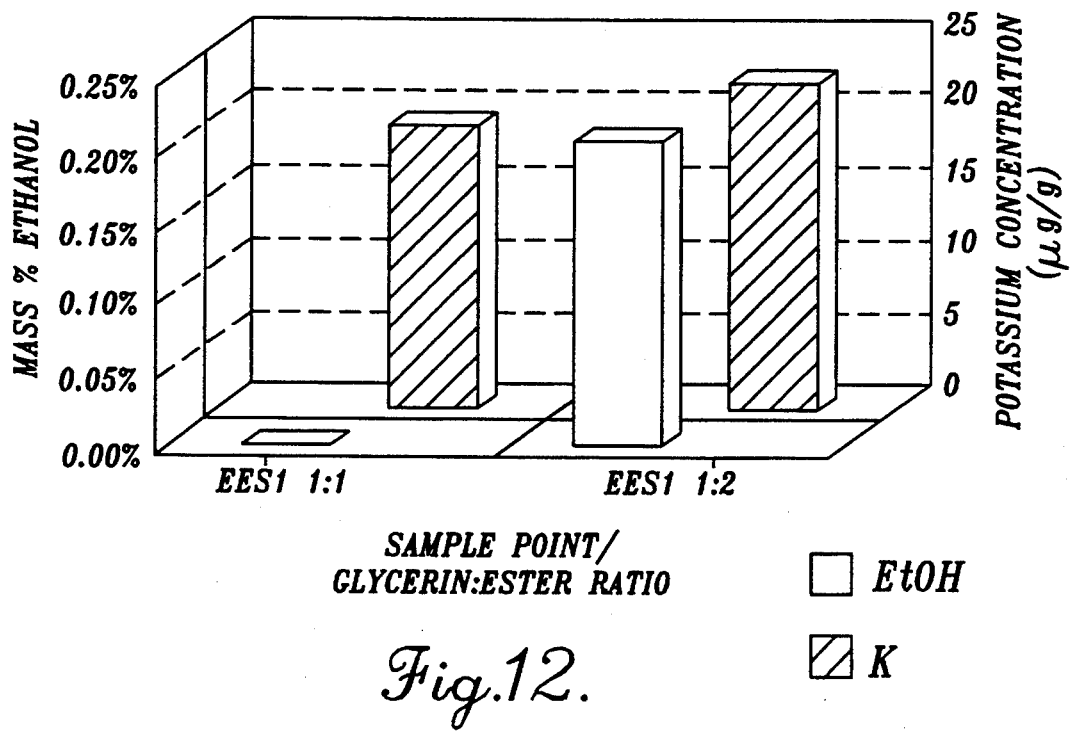
FIG. 12 is a graph illustrating the effect of glycerin to ester ratio on ethyl ester from settler No. 1.

FIG. 12 shows the effect of changing the ratio of glycerin added to the incoming ester to the composition of the ester leaving first settler 122. In all cases, nearly all of the detectable ethanol was removed in the first stage and the concentration of potassium was reduced more than 40 times. For the 1:2 glycerin to ester ratio slightly larger amounts of ethanol and potassium were detected. This may indicate that the lower glycerin to ester ratio is less effective in extracting the ethanol and potassium. However, the differences between the 1:1 and the 1:2 samples were small enough to be within sampling analysis error. This system was less prone to fluctuation than the methyl system because the ester used here was prepared in advance of the experiment and was of constant composition.

Figure 13:
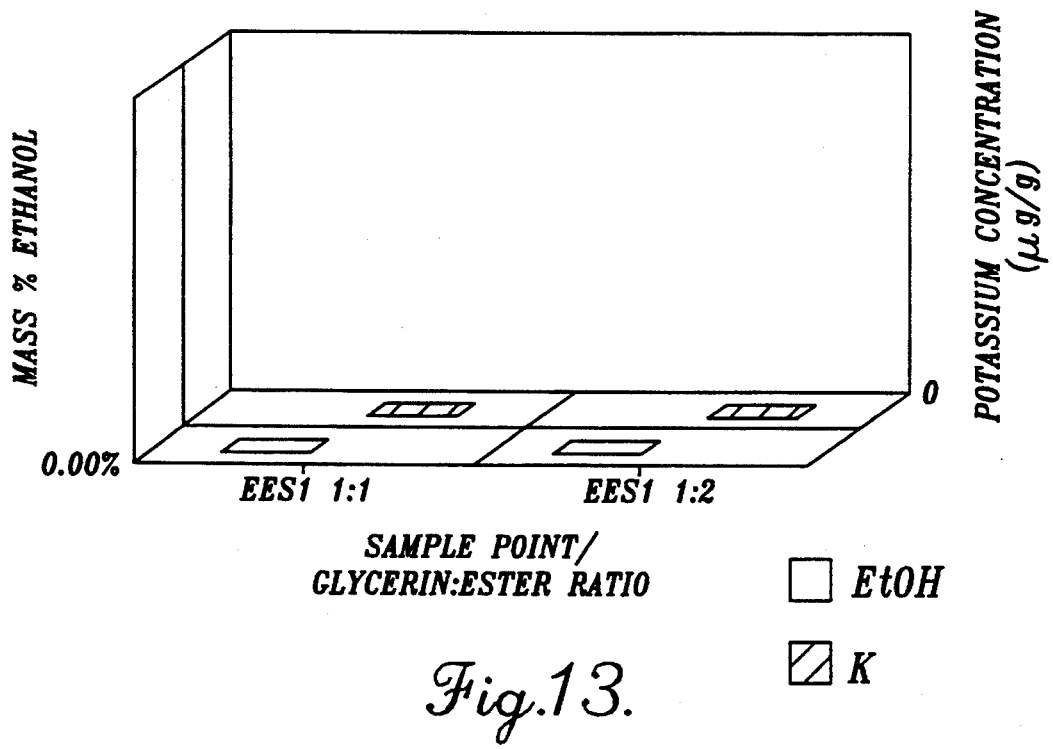
FIG. 13 is a graph illustrating the effect of glycerin to ester ratio on final ethyl ester product.

FIG. 13 is similar to FIG. 12 except that the fuel from second settler 124 or the final alcohol ester product is being analyzed. Here all concentrations have been reduced to below the detectable levels indicating that a much lower glycerin to ester ratio could be used, or one stage could be eliminated.

Figure 14:
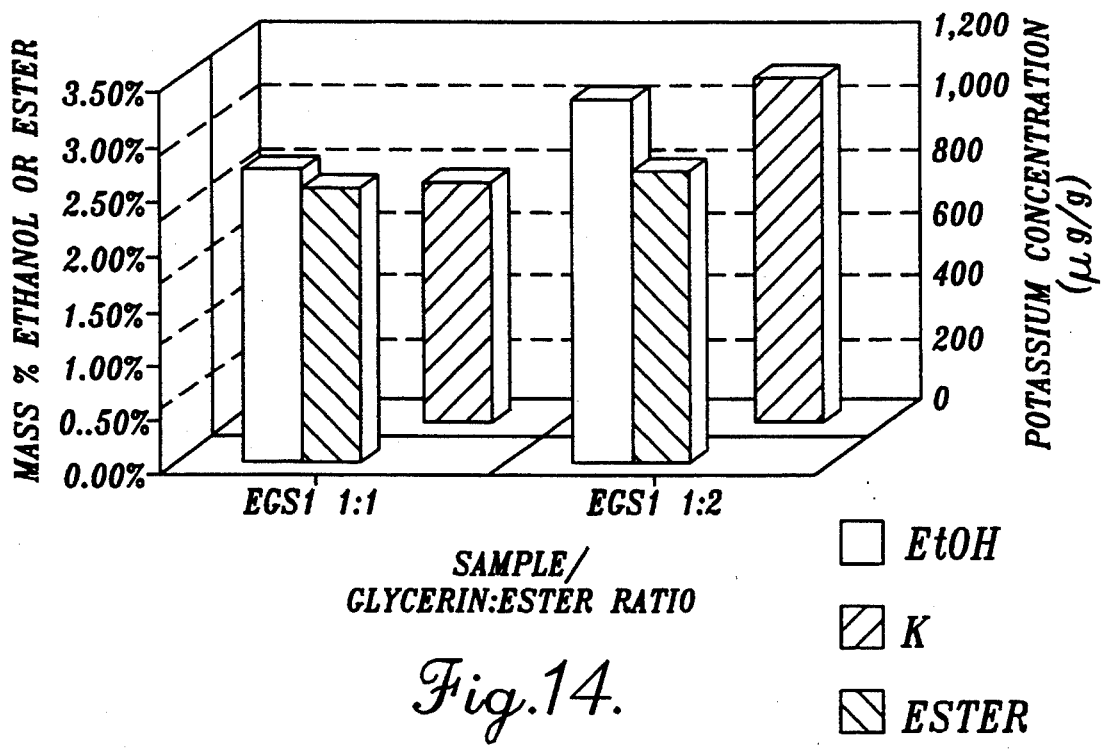
FIG. 14 is a graph illustrating the effect of glycerin to ethyl ester ratio on glycerin from settler No. 1.
Figure 15:
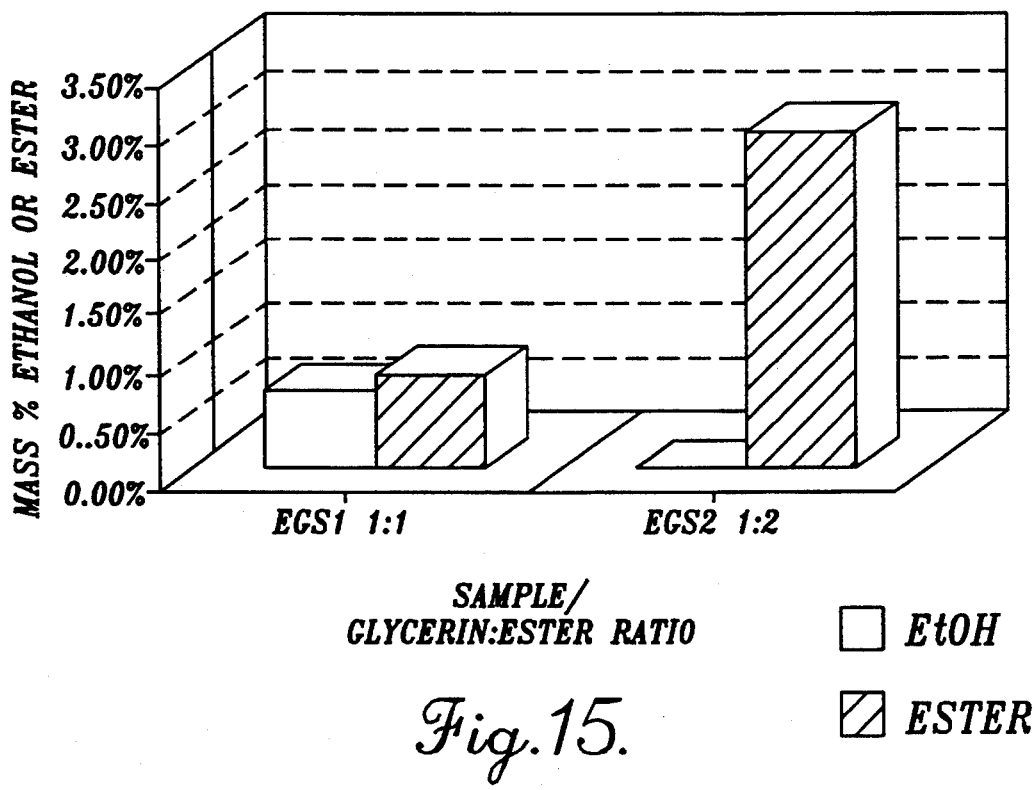
FIG. 15 is a graph illustrating the effect of glycerin to ethyl ester ratio on glycerin from settler No. 2.

FIG. 14 shows the concentrations of the glycerin from first settler 122. This FIGURE shows that the glycerin is extracting the ethanol and the potassium from the ester. It can also be seen that as the amount of glycerin added per amount of ester decreases, some carryover of the ester into the glycerin is observed. FIG. 15 also supports this observation (note that the glycerin from second settler 124 was not analyzed for potassium). One possible explanation would be that the settling time was not long enough to allow for a complete phase separation. Entrainment effects may also be a possible cause because of the extreme viscosity of glycerin. From previous observations, the samples shown in FIG. 15 appear to be reversed. Since there was some ethanol in the ester from first settler 122 for the 1:2 ratio, it would be expected that the glycerin from second settler 124 would contain some ethanol for the 1:2 ratio but not for the 1:1 ratio. These expectations are just the opposite.

Figure 16:
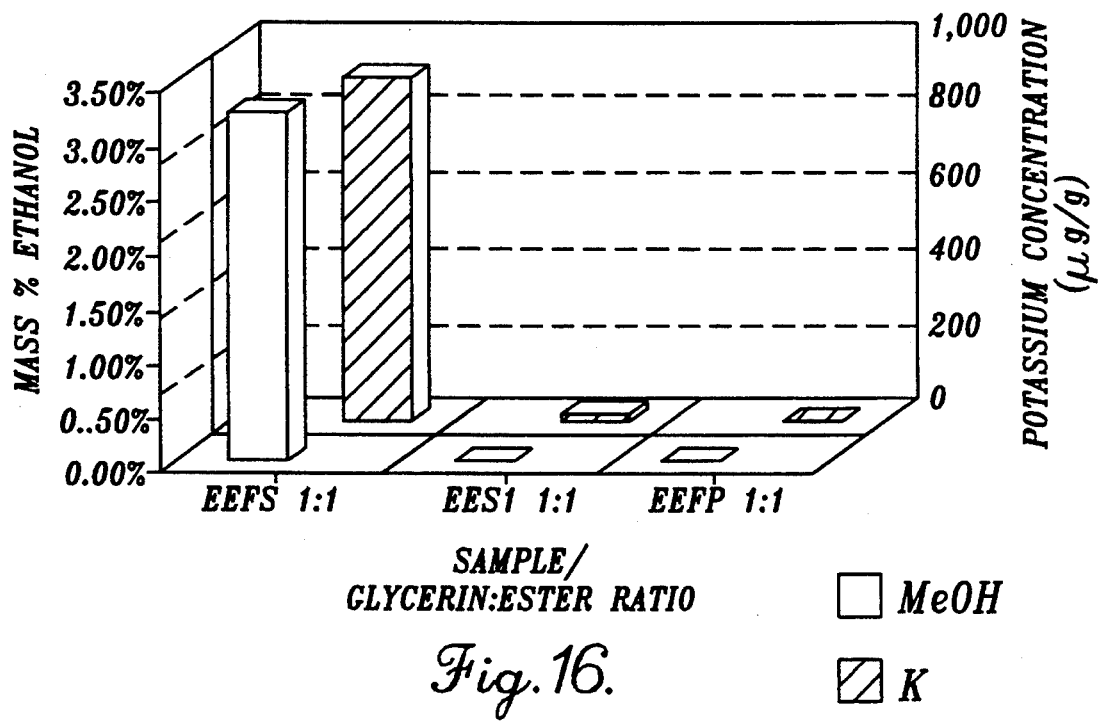
FIG. 16 is a graph illustrating concentration profile for 1:1 glycerin to ethyl ester ratio.
Figure 17:
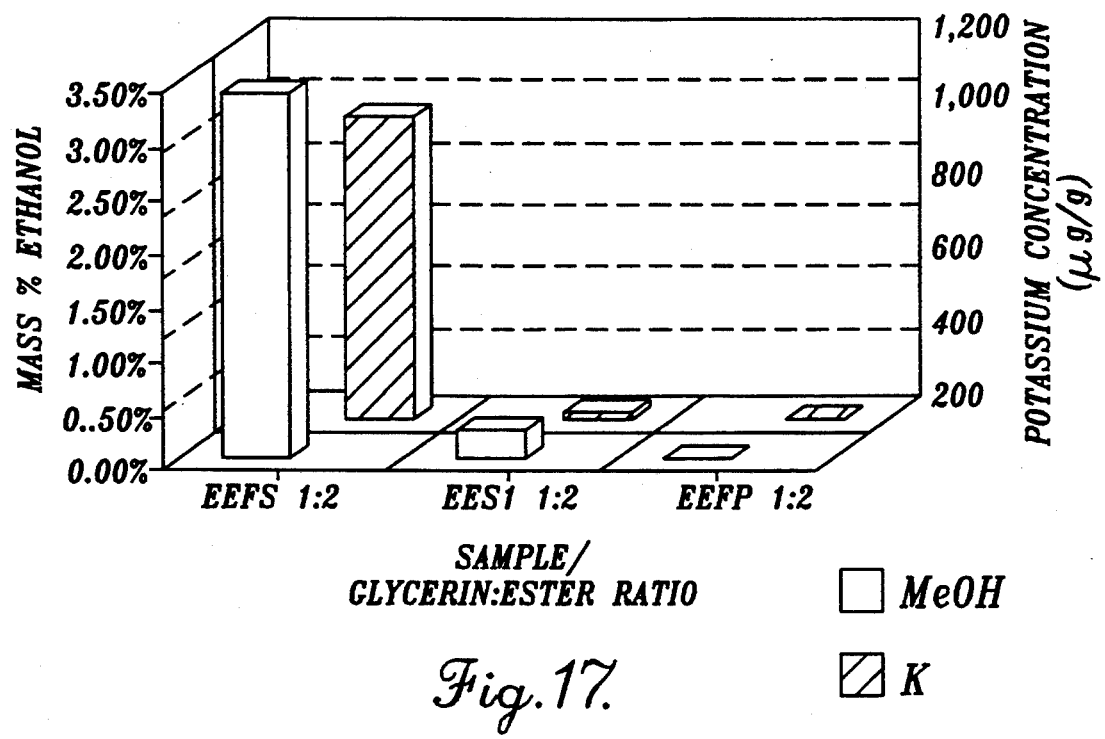
FIG. 17 is a graph illustrating the concentration profile for a 1:2 glycerin to ethyl ester ratio.

FIG. 16 and FIG. 17 show the change in ester concentration from the feed to first settler 122 to second settler 124. In all cases, a massive reduction in ethanol and potassium concentration is seen from the feed stock to the ester effluent from the first stage with the second stage making little contribution. These FIGURES illustrate the effectiveness of the glycerin extraction and suggest that one stage could be eliminated, or the ratio of glycerin to ester could be further reduced.

The examples show that the glycerin extraction process carried out in accordance with the present invention successfully removes excess alcohol and potassium from both methyl and ethyl esters. The continuous reactor worked well for the methyl ester, but obtaining a phase separation was difficult with the ethyl ester, and a continuous reactor would preferably be not at much higher percentages of excess alcohol and a larger settler would be required. The experimental results showed that all of the excess alcohol and most of the potassium was removed from the ester phase after the first stage even with a glycerin to ester ratio to 1:2. Because of this a one stage mixer-settler could be used to reduce capital investment, or a two stage mixer-settler could be used with a much lower glycerin to ester ratio which would reduce the operating cost.

Two phenomena were observed with the ethyl ester. First, the untreated ethyl ester settled a small amount of glycerin over a period of about three weeks. In the same period of time no glycerin was observed to settle out of the ethyl ester that had been purified in the mixer-settler. The absence of glycerin settling out of the ester is an indication of the high purity of the ethyl ester product produced in accordance with the present invention. Providing an ethyl ester product that does not settle out a small amount of glycerin is desirable from a materials-handling standpoint and the standpoint of a concern for product purity or degradation. Second, the ethyl ester purified in the mixer-settler did not emulsify nearly as severely as the untreated ethyl ester did. Providing a purified ethyl ester wherein the ethyl ester does not form a water emulsion may have advantages in high value added products where water emulsions are undesirable.

TABLE 1

Methyl Ester Run Results

| Sample # | Methanol Mass % | Glycerin Mass % | M. Ester Mass % | Potassium µg/g | Sodium µg/g | Sulfur µg/g |
|---|---|---|---|---|---|---|
| MEFS 1:1 | 3.36% | 0.00% | 96.64% | 440 | 12 | BDL |
| MEFS 1:1.5 | 2.44% | 0.00% | 97.56% | 270 | 14 | BDL |
| MEFS 1:2 | 3.82% | 0.00% | 96.18% | 280 | 15 | BDL |
| MGFS 1:1 | 46.42% | 49.93% | 3.66% | — | — | — |
| MGFS 1:1.5 | 52.32% | 47.68% | 0.00% | — | — | — |
| MGFS 1:2 | 48.57% | 51.43% | 0.00% | 36000 | 50 | 60 |
| MES1 1:1 | 0.00% | 0.00% | 100.00% | 20 | 30 | 34 |
| MES1 1:1.5 | 0.00% | 0.00% | 100.00% | 19 | 25 | BDL |
| MES1 1:2 | 0.00% | 0.00% | 100.00% | BDL | 60 | 40 |
| MGS1 1:1 | 1.90% | 98.10% | 0.00% | 260 | 10 | BDL |
| MGS1 1:1.5 | 2.67% | 97.33% | 0.00% | 780 | 10 | 5 |
| MGS1 1:2 | 2.63% | 92.80% | 4.57% | 440 | 11 | BDL |
| MGS2 1:1 | 0.00% | 100.00% | 0.00% | — | — | — |
| MGS2 1:1.5 | 0.00% | 95.28% | 4.72% | — | — | — |
| MGS2 1:2 | 0.00% | 82.51% | 17.49% | — | — | — |
| MEFP 1:2 | 0.00% | 0.00% | 100.00% | BDL | 13 | BDL |
| MEFP 1:1.5 | 0.00% | 0.00% | 100.00% | BDL | 44 | 25 |
| MEFP 1:2 | 0.74% | 0.00% | 99.26% | BDL | 15 | BDL |

— Indicates that the sample was not analyzed for that component.
BDL - Below detectable levels

TABLE 2

Ethyl Ester Run Results

| Sample # | Ethanol Mass % | Glycerin Mass % | E. Ester Mass % | Potassium µg/g | Sodium µg/g | Sulfur µg/g |
|---|---|---|---|---|---|---|
| EEFS 1:1 | 3.24% | 0.00% | 96.76% | 925 | 42 | BDL |
| EEFS 1:2 | 3.40% | 0.00% | 96.60% | 970 | 64 | 16 |

TABLE 2-continued

Ethyl Ester Run Results

| Sample # | Ethanol Mass % | Glycerin Mass % | E. Ester Mass % | Potassium µg/g | Sodium µg/g | Sulfur µg/g |
|---|---|---|---|---|---|---|
| EES1 1:1 | 0.00% | 0.00% | 100.00% | 20 | 42 | BDL |
| EES1 1:2 | 0.21% | 0.00% | 99.79% | 23 | 33 | BDL |
| EGS1 1:1 | 2.73% | 94.70% | 2.57% | 780 | 9 | BDL |
| EGS1 1:2 | 3.38% | 93.91% | 2.71% | 1100 | 12 | 31 |
| EGS2 1:1 | 0.65% | 98.55% | 0.80% | — | — | — |
| EGS2 1:2 | 0.00% | 97.02% | 2.98% | — | — | — |
| EEFP 1:1 | 0.00% | 0.00% | 100.00% | BDL | 50 | 30 |
| EEFP 1:2 | 0.00% | 0.00% | 100.00% | BDL | 45 | BDL |

— Indicates that the sample was not analyzed for that component.
BDL - Below detectable levels While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for purification of an alcohol ester of a triglyceride produced by a transesterification reaction between an alcohol and the triglyceride, the transesterification reaction occurring in the presence of a catalyst, the method comprising the steps:
    separating a first phase including the alcohol ester, unreacted alcohol, and catalyst from a second phase including a by-product alcohol, unreacted alcohol and catalyst;
    treating the second phase to separate the by-product alcohol from the unreacted alcohol and catalyst;
    treating the first phase with the separated by-product alcohol to separate the catalyst from the alcohol ester.

2. The method of claim 1, wherein treating the first phase also separates unreacted alcohol from the alcohol ester.

3. The method of claim 1, wherein treating the first phase further provides a collected mixture of unreacted alcohol and catalyst from the first phase and by-product alcohol.

4. The method of claim 3, further comprising the step of combining the second phase with the collected mixture from the step of treating the first phase,. and then treating the combination of the second phase and collected mixture to separate by-product alcohol from the untreated alcohol and catalyst.

5. The method of claim 3, wherein the collected mixture is treated to separate by-product alcohol from the unreacted alcohol, the method further comprising the step of recycling the unreacted alcohol separated from the by-product alcohol to the transesterification reaction.

6. The method of claim 5, wherein the unreacted alcohol is separated from the by-product alcohol by distillation.

7. The method of claim 5, wherein the by-product alcohol separated from the unreacted alcohol includes organic residue and catalyst, the method further comprising the step of separating the organic residue and the catalyst from the by-product alcohol after the by-product alcohol has been separated from the unreacted alcohol.

8. The method of claim 7, further comprising the step of oxidizing the organic residue and the catalyst separated from the by-product alcohol.

9. The method of claim 1, wherein treating the second phase comprises distilling the second phase.

10. The method of claim 1, further comprising the step of recycling by-product alcohol containing unspent catalyst to a vessel wherein the transesterification reaction is carried out.

11. The method of claim 1, wherein the by-product alcohol is glycerin.

12. The method of claim 1, further comprising the step of contacting the second phase with additional unreacted alcohol to produce additional alcohol ester and by-product alcohol.

13. The method of claim 1, further comprising the step wherein the second phase is heated to produce additional alcohol ester and by-product alcohol.

14. A method for the recovery of by-products from a transesterification reaction between an alcohol and a triglyceride in the presence of a catalyst, the method comprising the steps:
    separating a first phase including an alcohol ester of the triglyceride, first phase unreacted alcohol, and first phase catalyst from a second phase including a by-product alcohol, second phase unreacted alcohol and second phase catalyst;
    separating the second phase unreacted alcohol from the by-product alcohol and the second phase catalyst;
    separating the by-product alcohol from the second phase catalyst;
    treating the first phase with the by-product alcohol separated from the second phase catalyst to separate the first phase unreacted alcohol and the first phase catalyst from the alcohol ester and provide a mixture of the by-product alcohol, first phase unreacted alcohol, and the first phase catalyst;
    combining the mixture of the by-product alcohol, first phase unreacted alcohol and first phase catalyst with the second phase after it is separated from the first phase; and
    separating the combined mixture into streams of by-product alcohol, first and second phase unreacted alcohol, and first and second phase catalyst.

15. A method for purification of an alcohol ester of a triglyceride produced by a transesterification reaction between an alcohol and the triglyceride, the transesterification reaction occurring in the presence of a catalyst, the method comprising the steps:
    separating a first phase including the alcohol ester, unreacted alcohol, and catalyst from a second phase including a by-product alcohol, unreacted alcohol, and catalyst;
    treating the first phase with a recovery alcohol to separate the catalyst from the alcohol ester.

16. The method of claim 15, wherein the recovery alcohol is glycerin.

17. A method for the recovery of by-products from a transesterification reaction between an alcohol and a triglyceride in the presence of a catalyst, the method comprising the steps:
   separating a first phase including an alcohol ester of the triglyceride, first phase unreacted alcohol, and first phase catalyst from a second phase including a by-product alcohol, second phase unreacted alcohol and second phase catalyst;
   treating the first phase with a recovery alcohol to separate the first phase unreacted alcohol and the first phase catalyst from the alcohol ester and provide a mixture of the recovery alcohol, first phase unreacted alcohol, and the first phase catalyst; and
   separating at least one component from the mixture of the recovery alcohol, first phase unreacted alcohol, and the first phase catalyst.

18. The method of claim 17, wherein the recovery alcohol is glycerin.

19. The method of claim 1, wherein the unreacted alcohol separated from the by-product alcohol during treating of the second phase is recycled to the transesterification reaction.

20. The method of claim 19, wherein the by-product alcohol separated from the unreacted alcohol includes organic residue and catalyst, the method further comprising the step of separating the organic residue and the catalyst from the by-product alcohol after the by-product alcohol has been separated from the unreacted alcohol.

21. The method of claim 20, further comprising the step of oxidizing the organic residue and the catalyst separated from the by-product alcohol.

22. A method for the recovery of by-products from a transesterification reaction between an alcohol and a triglyceride in the presence of a catalyst, the method comprising the steps:
   separating a first phase including an alcohol ester of the triglyceride, first phase unreacted alcohol, and first phase catalyst from a second phase including a by-product alcohol, second phase unreacted alcohol and second phase catalyst.
   treating the first phase with a recovery alcohol to separate the first phase unreacted alcohol and the first phase catalyst from the alcohol ester and provide a mixture of the recovery alcohol, first phase unreacted alcohol, and the first phase catalyst; and
   separating at least one component from the by-product alcohol, second phase unreacted alcohol and second phase catalyst that form the second phase.

23. The method of claim 22, wherein the recovery alcohol is glycerin.

24. The method of claim 1, wherein the second phase further comprises water, the method further comprising the step of separating the water from the by-product alcohol of the second phase.

25. The method of claim 14, wherein the second phase further comprises water, the method further comprising the step of separating the water from the by-product alcohol of the second phase.

26. The method of claim 17, wherein the second phase further comprises water, the method further comprising the step of separating the water from the by-product alcohol of the second phase.

27. The method of claim 22, wherein the second phase further comprises water, the method further comprising the step of separating the water from the by-product alcohol of the second phase.

28. A method for purification of an alcohol ester comprising the step:
   treating the alcohol ester with a recovery alcohol to extract impurities from the alcohol ester into the recovery alcohol.

29. The method of claim 28, wherein the recovery alcohol is glycerin.

* * * * *

UNITED STATES PATENT AND TRADEMARK OFFICE
CERTIFICATE OF CORRECTION

PATENT NO. :   5,424,467
DATED      :   June 13, 1995
INVENTOR(S) :  N. Bam et al.

It is certified that error appears in the above-indentified patent and that said Letters Patent is hereby corrected as shown below:

| COLUMN | LINE |  |
|---|---|---|
| 2 | 17 | "byproduct" should read --by-product-- |
| 15 (Claim 4, | 44 line 3) | "phase,." should read --phase,-- |

Signed and Sealed this

Nineteenth Day of September, 1995

Attest:

BRUCE LEHMAN

*Attesting Officer*      *Commissioner of Patents and Trademarks*